United States Patent [19]

Shiratori et al.

[11] Patent Number: 4,569,826
[45] Date of Patent: Feb. 11, 1986

[54] GAS DETECTING ELEMENT

[75] Inventors: Masayuki Shiratori, Kawasaki; Tadashi Sakai, Yokohama; Masaki Katsura, Yokosuka; Osamu Takikawa, Kamakura, all of Japan

[73] Assignee: Kabushiki Kaisha Toshiba, Japan

[21] Appl. No.: 625,127

[22] Filed: Jun. 27, 1984

[30] Foreign Application Priority Data

Jun. 27, 1983 [JP] Japan ................................ 58-114232
Jan. 17, 1984 [JP] Japan .................................... 59-4742

[51] Int. Cl.$^4$ ............................................. G01N 27/12
[52] U.S. Cl. .......................................... 422/90; 73/23; 324/71.5; 422/98
[58] Field of Search ...................... 73/23; 324/71 SN; 422/90, 94–98; 338/34

[56] References Cited

U.S. PATENT DOCUMENTS 4,352,286 10/1982 Nakatani et al. ........................ 73/23

FOREIGN PATENT DOCUMENTS 46989 3/1982 European Pat. Off. .............. 422/98
22995 2/1977 Japan ..................................... 422/98

OTHER PUBLICATIONS

Ohno, Chemical Abstracts, vol. 96, 1981, No. 96:14262f.

Primary Examiner—Arnold Turk
Attorney, Agent, or Firm—Banner, Birch, McKie & Beckett

[57] ABSTRACT

A gas detecting element comprises a substrate, a gas sensitive body provided on the substrate, a pair of electrodes connected to the gas sensitive body and a catalyst layer provided on the surface of the gas sensitive body. The catalyst layer including a carrier material and a catalyst material of copper and tungsten. The gas detecting element in accordance with the present invention has equal sensitivity to a number of different gases.

10 Claims, 11 Drawing Figures

GAS DETECTING ELEMENT

BACKGROUND OF THE INVENTION

This invention relates to a gas detecting element, and more particular, is directed to a gas detecting element with a catalyst layer.

Various researches have developed a gas detecting element using a gas sensitive body, such as $SnO_2$ type oxide. The resistance value of the body changes when it comes into contact with gases. Such a gas detecting element employs a catalyst in order to enhance its detecting sensitivity. In one example of a gas detecting element, the catalyst layer is provided on the gas sensitive body. The gas detecting element, the material of the gas sensitive body and the catalyst layer are generally selected in order that the gas detecting element has a specific sensitivity for one particular gas, such as CO gas. The catalyst layer is a thick film formed by a mixture of a carrier material with a noble metal such as platinum (Pt), Palladium (Pd). In a gas detecting element employing the catalyst layer described above, the sensitivity of the element is enhanced, but the sensitivity is adversely affected by humidity. The sensitivity deteriorates after the element is kept under high humidity for a long time. Where the gas detecting element is used for detecting a dangerous gas, such as CO gas, the defects of the element described above becomes a very serious problem. Thus, a gas detecting element unaffected by humidity is greatly desired.

With the present trend toward the use of more and more electronics in residential homes, many homes now use a ventilation system that automatically ventilates a room by a control signal from a gas detecting element. The gas detecting element which is used for the ventilation system should have the following characteristics.

(1) The gas detecting element should be highly sensitive to all gases which are dangerous or iritating to humans.
(2) The gas detecting element should have a quick response characteristic and a quick release characteristic.
(3) The gas detecting element should have an excellent resistance to humidity.

If a gas detecting element has high sensitivity to only one kind of gas, it is difficult to establish a threshold value for generating switching signals. Thus, a gas detecting element should have uniform sensitivity to all types of gases to be detected. When the concentration of the gas to be detected exceeds a predetermined concentration, the gas detecting element should quickly change its resistance value so as to generate a control signal. Likewise, when the concentration of the gas to be detected decreases below a predetermined concentration, the gas detecting element should quickly return to its original resistance value.

It is also important that the gas detecting element have excellent resistance to humidity so that the element can be used under various environmental conditions. Furthermore, if the gas detecting element is not operated continuously, it is also desirable that the element quickly return to a stable state when it is again used.

The gases to be detected by the gas detecting element for ventilation purposes include CO (carbon monoxide) gas, tobacco smoke, alcohol, etc. The conventional gas detecting element employing a noble metal, such a plantinum (Pt), palladium (Pd), etc. as a catalyst material, does not have sufficient desirable detecting characteristics for a ventilation system because the sensitivity of the gas detecting element to tobacco smoke is very low. Moreover, the element does not exhibit good resistance to humidity.

Japanese patent disclosure No. 58-118953, which was published on July 15, 1983, discloses a gas detecting element having a gas sensitive body mixed with a catalyst material consisting of a carrier material of $TiO_2$ and a catalyst material of W (tungsten) in order to enhance its sensitivity for detecting propane gas, gas consisting of methane gas as a main component and CO (carbon monoxide) gas. The element is deficient, however, with respect to uniformity of sensitivity, humidity resistance, and stability.

SUMMARY OF THE INVENTION

It is an object of the present invention to provide a gas detecting element with uniform sensitivity for detecting all gases to be ventilated from a room.

It is a further object of the invention to provide a gas detecting element which has excellent resistance to humidity.

It is another object of the invention to provide a gas detecting element with good sensitivity for detecting tobacco smoke.

It is another object of the invention to provide a gas detecting element with quick response and quick release characteristics.

It is a still further object of the invention to provide a gas detecting element suitable for use in a ventilation system.

The aforementioned objects are achieved in accordance with the present invention by using a new and improved catalyst layer for the gas detecting element.

A gas detecting element according to one aspect of the invention comprises a substrate, a gas sensistive body provided on the substrate, a pair of electrodes in contact with the gas sensitive body and a catalyst layer provided on the surface of the gas sensitive body including a carrier material and a catalyst material of copper and tungsten. The gas detecting element according to this aspect of the invention has a catalyst layer which is provided on the gas sensitive body and includes a carrier material of aluminum oxide and a catalyst material of copper and tungsten oxide. It has been discovered that a catalyst layer which includes a catalyst material of copper and tungsten can be used to form a gas detecting element with good sensitivity for all types of gases to be detected, i.e., carbon monoxide gas, alcohol, and tobacco smoke, equally.

A level of CO gas above 200 ppm is considered dangerous to human life and a level of tobacco smoke above 500 ppm is considered an irritant to non-smokers. According to this aspect of the invention, the sensitivity ratio of the detector element to tobacco smoke and CO gas is 0.9 to 1.1. Thus, the sensitivity of the detector element to CO gas and tobacco smoke are substantially equal. The element is, therefore, suitable for a ventilation system. Also, the element has good sensitivity for other kinds of gases to be detected, such as alcohol (its detecting standard is about 50 ppm), which is about the same sensitivity as CO gas.

While the conventional gas detecting element with a catalyst material of Pd cannot detect gas because the resistance value of the element is unstable after it is kept at a high humidity (at 90 RH% and at room temperature), the gas detective element with a catalyst material of copper and tungsten in accordance with the present invention is not affected by humidity.

The response and release characteristics of the element of the invention are excellent compared with those of a conventional element. The response and release characteristics of the element of the invention are less than one minute and less than three minutes, respectively. The response and release characteristics of the conventional element are three minutes and ten minutes, respectively.

The humidity resistance characteristics of the gas detecting element in accordance with the present invention is extremely enhanced and the sensitivity is also enhanced by using a catalyst layer including copper sulfate ($CuSO_4$). Further, the response and release characteristics of an element using $CuSO_4$ are improved when compared with the conventional element. However, an element with a catalyst material of copper sulfate alone does not have sufficient sensitivity for detecting tobacco smoke. Thus, according to one aspect of the invention, a gas detecting element with a high sensitivity for detecting tobacco smoke is realized by using a catalyst layer including a catalyst material of copper and tungsten.

Although copper and tungsten are added to the catalyst layer in various kinds of compounds such as oxide etc., the amount of catalyst material, by converting into copper and tungsten, ranges from 0.1 to 30 wt% of the amount of carrier material. If the amount of catalyst material is less than 0.1 wt%, the catalyst layer cannot work well as a catalyst. On the other hand, if the amount of catalyst material is more than 30 wt%, the catalyst layer is deteriorated.

Further, an atomic ratio of the amount of the tungsten atom to the amount of the copper atom (referred to as W/Cu hereafter), preferably ranges from 0.1 to 10. As previously explained, a gas detecting element to be used as a sensor for a ventilation system requires that it has good sensitivity for all types of gases to be detected. For example, the ratio of the sensitivity to tobacco smoke to the sensitivity for CO gas (referred to as Ssm/Sco hereafter, where S is sensitivity, sm is smoke and co is carbon monoxide), is preferably one. Thus, Ssm/Sco=1. As the gas detective sensor tends to be more sensitive to CO gas than tobacco smoke, the ratio of Ssm/Sco preferably falls within the range of 0.8 to 1. If the atomic ratio of W/Cu is less than 0.1 in the catalyst layer and the ratio of Ssm/Sco is less than 0.8 then the element cannot detect tobacco smoke because the amount of tungsten is too small. On the other hand, if the ratio of W/Cu exceeds 10, the sensitivity to gases is weakened.

The catalyst layer of the invention containing material of copper and tungsten may be prepared in the following manner. First, a predetermined amount of $Al_2O_3$ is dipped in a solution containing crystalline copper sulfate ($CuSO_4.5H_2O$) and ammonium paratungstate ($(NH_4)_{10}W_{12}O_{41}.5H_2O$). After the solution is stirred and mixed, it is dried for 1 to 2 hours under low pressure and is also dried by heating at a temperature of 100° C. The resultant dried material is pulverized and is calcined in a quartz crucible at a temperature of 400° to 600° C. Finally, the catalyst material is obtained. A slurry containing the catalyst material is prepared by mixing the catalyst material with a binder, such as aluminum hydroxy chloride. After the slurry is coated on the gas sensitive body to a predetermined thickness and is dried, it is calcined at a temperature of 400° to 500° C. The calcined temperature is preferably less than 600° C. because the decomposition temperature of $CuSO_4$ is about 650° C. It is considered that W is changed to tungsten oxide (WOx) during calcining.

If it is not necessary that the gas detecting element have a sensitivity to tobacco smoke, the gas detecting element, which has an excellent humidity resistant characteristics and a good sensitivity for detecting a reduction gas, such as CO gas, may be obtained by using copper sulfate ($CuSO_4$) alone as a catalyst material. Thus, the gas detecting element according to another aspect of the invention comprises a substrate, a gas sensitive body provided on the substrate which changes its resistance value when it contacts with a gas to be detected, a pair of electrodes contacted with the gas sensitive body, and a catalyst layer provided on the surface of the gas sensitive body which includes carrier material and a catalyst material of copper sulfate ($CuSO_4$). A catalyst layer including a carrier material of aluminum oxide ($Al_2O_3$) and a catalyst material of copper sulfate ($CuSO_4$) are the preferred combination for the element. A catalyst layer including a catalyst material of copper sulfate can enhance the humidity resistance characteristics of the gas detecting element. The excellent humidity characteristics of the gas detecting element of the invention is believed to be due to the fact that a catalyst material of copper sulfate ($CuSO_4$) changes to stable hydrate salt ($CuSO_4.5H_2O$) when it absorbs humidity in the atmosphere and the hydrate salt changes to anhydrous salt when it is heated. Thus, the gas detecting element is not affected by humidity.

A gas detecting element with the catalyst layer explained above also has a high sensitivity to CO gas compared to the sensitivity of the conventional gas detecting element.

The catalyst layer according to another aspect of the invention is prepared in the following manner.

First, a predetermined amount of $Al_2O_3$ is dipped in a solution containing crystalline copper sulfate ($CuSO_4.5H_2O$). After the solution is stirred and mixed, it is dried for 1 to 2 hours under low pressure and is also dried by heating at a temperature of 100° C. The resultant dried material is pulverized and is calcined in a quartz crucible at a temperature of 400° to 600° C. Finally, the catalyst material is obtained. The slurry containing the catalyst material is mixed with a binder, such as aluminum hydroxy chloride. After the slurry is coated on the gas sensitive body to a predetermined thickness and dried, it is calcined at a temperature of 400° to 500° C., and thus the catalyst layer is obtained. The calcined temperature is preferably less than 600° C. because the decomposition temperature of $CuSO_4$ is about 650° C.

$SiO_2$, $ZrO_2$, $Al_2O_3$, and any combination thereof may be used as a carrier material. $Al_2O_3$ is, however, preferable from the view point of resistance to humidity.

In the catalyst layer, the amount of $CuSO_4$ is preferably about 0.1 to 30 wt% of the amount of carrier material by converting into copper. If the amount of $CuSO_4$ is out of this range, it is not effective in enhancing sensitivity.

Materials which include copper, such as copper sulfate ($CuSO_4$), copper chloride ($CuCl_2$), and copper nitrate ($CuNO_3$) may be used, but $CuSO_4$ is preferred because a gas detecting element containing $CuSO_4$ in the catalyst layer has excellent stability with respect to humidity. The thickness of the catalyst layer is preferably 10 to 50 microns. If the thickness is outside of this range, the sensitivity of the element will be deteriorated.

The gas detecting element of this invention is prepared in the following manner. A pair of electrodes made from a conductive material, such as Au, Pt, etc., are formed on a heat-proof and insulative substrate made of ceramic, such as $Al_2O_3$ etc., by a screen printing method, sputtering or vapor deposition. The electrodes are provided opposite each other so that they contact with the gas sensitivity body. The electrodes may be provided between the substrate and the gas sensitive body or between the gas sensitive body and the catalyst layer. A cylindrical substrate or a plate substrate may be used for the substrate. When a cylindrical substrate is used, the gas sensitive body may be provided on an outer surface of the cylindical substrate.

A gas sensitive body is provided on the substrate having the electrodes. As the oxide semiconductor to be used for the gas sensitive body, there may be employed $SnO_2$ type, $In_2O_3$ type, $Fe_2O_3$ type and ZnO type semiconductors which will change their resistance value when they contact with a gas to be detected. The $SnO_2$ type, $In_2O_3$ type, $Fe_2O_3$ type and ZnO type semiconductors comprise $SnO_2$, $In_2O_3$, $Fe_2O_3$ and ZnO as the main component, respectively, and may optionally incorporate auxillary components such as $Nb^{5+}$, $Sb^3$, $Sb^{5+}$, etc. The gas sensitive body may be prepared by sputtering, vapor deposition, sintering or pyrolysis of an organic compound of a metal. From the view point of gas sensitivity, productivity, and endurance of the gas detecting element, the gas sensitive body may be preferably of a thin film prepared by sputtering and pyrolysis. The gas sensitive material is preferably made of $SnO_2$ type material to improve gas sensitivity.

In general, because the gas detecting element is heated by a heater during operation, the thin film type gas sensitive body is better than the thick film type because the thin film type has less thermal capacity. Further it has good response and release characteristics compared with the thick film type. In the case of the thin film type, the thickness of the gas sensitive body may be preferably 0.1 to 1 micron. If the thickness is thicker than 1 micron, the sensitivity will be deteriorated. On the other hand, if the thickness is thinner than 0.1, the sensitivity will be deteriorated and will also be unstable. The thin film is prepared in the following manner, for example.

First, an organic compound containing Sn such as metal salt of tin (e.g. tin-2 ethylhexanoate) or a resin salt contains Sn, an alkoxide of tin (ROSn, where R is an alkyl group), further an organometallic compound of tin (RSn, where R is an alkyl group or an aryl group), etc., or organic compound which contains Nb or Sb is dissolved in a suitable solvent such as toluene, benzene n-butyl alcohol, etc., to prepare a sample solution of a desired Sn concentration. The Sn concentration may be preferably within the range of from 1.0 to 20 wt%.

Next, the sample solution is coated on the surface of a substrate having a pair of electrodes, left to stand in the air for a predetermined period of time (usually 30 minutes to one hour) and then heated at an appropriate temperature (usually about 120° C.) to vaporize the solvent. The whole assembly is then baked in the air at a temperature of 400° to 700° C. for one half to one hour, whereby the organic compound containing Sn is pyrolyzed and at the same time Sn is oxidized to form a $SnO_2$ thin film. By repeating the coating and baking step several times, which cannot be determined precisely but varies depending on the Sn concentration in the sample solution employed, for example, about 1 to 4 times, a $SnO_2$ thin film with a desired film thickness is formed. When a thin film having Nb or Sb is prepared, either one of the Nb or Sb acts as donor. Nb or Sb may preferably be added to a content within the range from 0.005 to 0.05 in terms of the atomic ratio to Sn (Nb/Sn or Sb/Sn). The catalyst layer is then prepared on the gas sensitive body as explained above.

In general, a gas detecting element has a heater which controls its temperature of operation in order to improve its sensitivity. In the case of a cylindrical substrate, the heater may be disposed in the substrate. In case of a plate substrate, the heater may be provided on a back surface of the substrate opposite to a front surface on which the gas sensitive body is coated or the heater may be provided under the gas sensitive body separated from the body by an insulating layer.

DETAILED DESCRIPTION OF THE PREFERRED EMBODIMENT

Referring now to the drawings, the present invention will be explained in detail.

Figure 1:
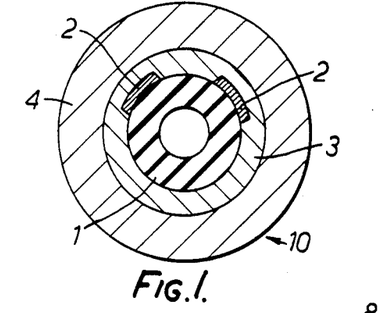
FIG. 1 is a sectional view of one preferred embodiment of the invention.

FIG. 1 shows a sectional view of the preferred embodiment of the invention in which a gas detecting element (10) comprises a cylindrical substrate (1) made of insulating material, a pair of electrodes (2), provided on an outer surface of the substrate (1) so that each of the electrodes extends along the length direction of the substrate (1), a gas sensitive body (3) provided on the substrate (1) so as to cover the electrodes (2), and a catalyst layer (4) covering the gas sensitive body (3). The gas sensitive body (3) with a thickness of about 0.3 micron essentially consists of $SnO_2$. The catalyst layer (4) with a thickness of 20 microns essentially consist of a carrier material of $Al_2O_3$ and catalyst material both of copper sulfate ($CuSO_4$) and tungsten oxide ($WO_x$).

Figure 2:
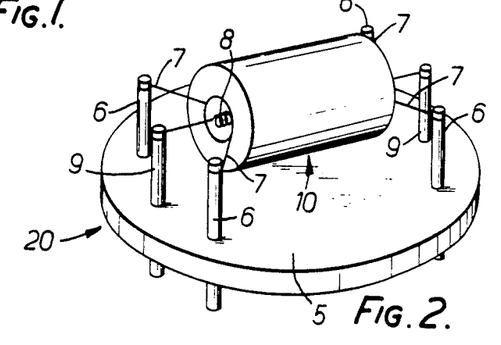
FIG. 2 is a perspective view of a gas sensor using the gas detecting element of the invention.

The gas detecting element (10) of the invention is assembled into a gas sensor (20) as shown in FIG. 2. The gas detecting element (10) is supported by lead wires (7), each of which has one end connected with an electrode (2) and another end connected with a pin (6) of a stem (5). A heater (8), which is suspended between pins (9) of the stem (5), is provided in the element (10) in order to heat and keep the element at operating temperature. The gas sensor (20) also has a cap (not shown) made of a metal screen in order to prevent the gas detecting element (10) from being contaminated.

The gas detecting element explained above is prepared in the following manner. First, a predetermined amount of tin-2 ethylhexanoate is dissolved in a solution of n-butanol such that 10 wt% of the tin is contained in the solution. For an impurity of Nb and Sb, Nb-resinate and antimony n-butylate ((n-OC$_4$H$_9$)$_3$Sb) are dissolved into the solution so that the atomic ratio of Sb to Sn is 0.1. The solution containing Sn, Nb, and Sb is coated on the outer surface of the cylindrical substrate (1) having the electrodes (3), and the substrate (1) is left in an air atmosphere for one hour. Then, the substrate (1) is heated at a temperature of 120° C. in order to vaporize the n-butanol. Further, it is calcined in an air atmosphere at a temperature of 400° C. for one hour. The steps of coating and calcining explained above are repeated three times, and then the gas sensitive body (3) essentially consisting of SnO$_2$ is prepared. The thickness of the body (3) is about 0.3 microns.

Next, the catalyst layer is prepared in the following manner. CuSO$_4$.5H$_2$O and (NH$_4$)$_{10}$W$_{12}$O$_{41}$.5H$_2$O are dissolved in water, and then, Al$_2$O$_3$ powder with a surface area of 100 m$^2$/g is added to the solution. Al$_2$O$_3$ powder is than taken out of the solution by a filter and the powder is dryed under low pressure for one and one half hours. The powder is pulverized in a mortar and the resultant powder is then calcined in a quartz crucible at a temperature of 400° C. By using the catalyst powder, the catalyst layer is prepared in the same manner as explained above.

The sensitivity of the gas detector is measured as a ratio of Rair/Rgas by using CO gas with a concentration of 200 ppm and smoke with a concentration of 500 ppm. During the measurement, the gas detecting element at about 350° C. As previously explained, a larger value of Rair/Rgas means a higher sensitivity. The measurement of CO gas is carried out by putting a predetermined amount of CO gas in a measurement tank. The measurement of smoke is carried out in the following manner. Smoke is collected together with air by exhaling into an injector at an exhalation rate of an ordinary smoker. The collected smoke (mixture of smoke and air) is injected into a measurement tank. The result of the measurement is shown in Table 1.

catalyst layer (shown as Comparison No. 1 in Table 1) has poor sensitivity for smoke. On the other hand, the gas detecting element containing only tungsten in the catalyst layer (shown as Comparison No. 2) has good sensitivity for CO gas.

Figure 3A:
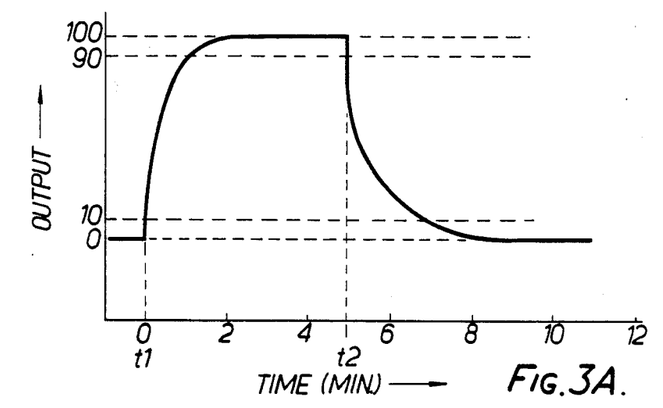
FIG. 3A is a graph showing response and release characteristics of the element of the invention.
Figure 3B:
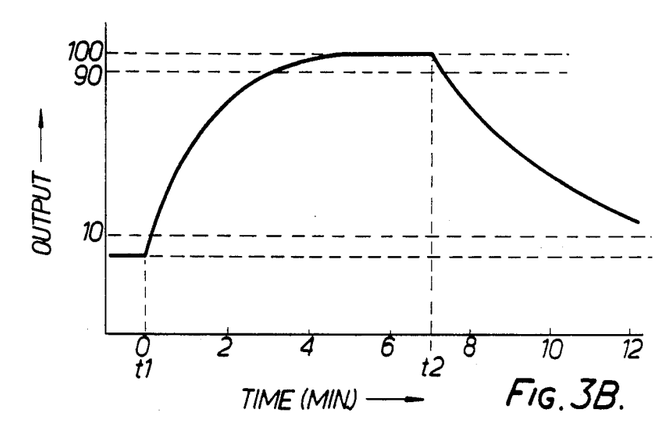
FIG. 3B is a graph showing response and release characteristics of the element of comparison examples.

The response and release characteristics of the gas detecting element Example 4 shown in Table 1 is measured and the result of the measurement is shown in FIG. 3A. In order to compare these characteristics, the characteristics of the gas detecting element comprising a gas sensitive body of SnO$_2$ and a catalyst layer consisting of Al$_2$O$_3$ as a carrier and Pd (referred to as Comparison No. 3 hereafter) is measured and the result of the measurement is shown in FIG. 3B. In FIGS. 3A and 3B, the gas to be detected is injected at time t1 and is exhausted at time t2. The response time is the period from the time when the gas is injected to the time when the output of the gas detecting element increases to 90% of saturated output. The release time is the time period from the time when the gas is exhausted to the time when the output of the element decreases to 10% of saturated output. As seen from FIGS. 3A and 3B, the response time and the release time of the gas detecting element of the invention are one minute and three minutes, respectively, but those of the gas element of Comparison No. 3 are three minutes and ten minutes, respectively. Thus, the response and release characteristics of the gas detecting element of the invention is excellent in comparison.

The gas detecting element of Example 4 takes only three minutes from applying voltage to the heater to generating a stable output, but the gas detecting element of Comparison No. 3 requires more than one hour from the application of voltage to the heater to generating a stable output. Thus, the gas detecting element of the invention may be used as a ventilation sensor which requires that the sensor be settled to a stable condition immediately after voltage is applied to it.

Figure 4:
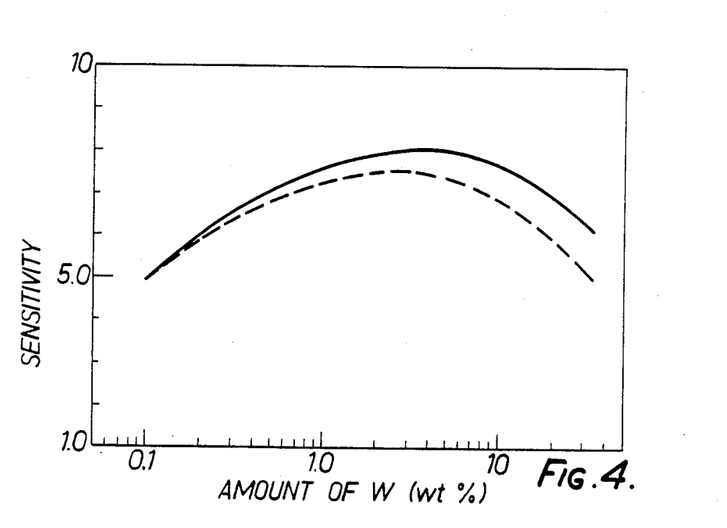
FIG. 4 is a graph showing sensitivity characteristics.

The sensitivity of a gas detecting element containing copper and tungsten, of which the ratio of W/Cu is 2 (that is, W/Cu=2), for CO gas with a concentration of 200 ppm and tobacco smoke with a concentration of 500 ppm is shown in FIG. 4 in accordance with the amount of tungsten. In FIG. 4, a solid line and dotted line show the sensitivity characteristics for CO gas and tobacco smoke, respectively. As seen from FIG. 4, when the

TABLE 1

| Sample No. | Total Amount of Catalyst Material (wt %) | Amount of Catalyst Material | | Sensitivity | | | Sensitivity Ratio Ssm/Sco |
|---|---|---|---|---|---|---|---|
| | | Cu(wt %) | W(wt %) | CO(200 ppm) | Smoke of Tobacco (500 ppm) | Ethanol (50 ppm) | |
| Example 1 | 20.1 | 0.1 | 20.0 | 5.0 | 6.5 | 6.8 | 1.3 |
| Example 2 | 10.5 | 0.5 | 10.0 | 6.8 | 7.5 | 7.7 | 1.1 |
| Example 3 | 6.0 | 1.0 | 5.0 | 8.5 | 8.5 | 9.5 | 1.0 |
| Example 4 | 4.5 | 1.5 | 3.0 | 8.1 | 7.6 | 9.8 | 0.94 |
| Example 5 | 4.0 | 2.0 | 2.0 | 8.0 | 7.4 | 9.6 | 0.93 |
| Example 6 | 6.0 | 5.0 | 1.0 | 7.6 | 6.1 | 9.4 | 0.80 |
| Example 7 | 10.5 | 10.0 | 0.5 | 6.9 | 5.3 | 8.0 | 0.77 |
| Example 8 | 20.1 | 20.0 | 0.1 | 5.6 | 4.0 | 7.3 | 0.71 |
| Comparison 1 | 5.0 | 5.0 | 0 | 8.0 | 4.8 | 10.1 | 0.63 |
| Comparison 2 | 5.0 | 0 | 5.0 | 5.0 | 8.3 | 10.5 | 1.7 |

Figure 5A:
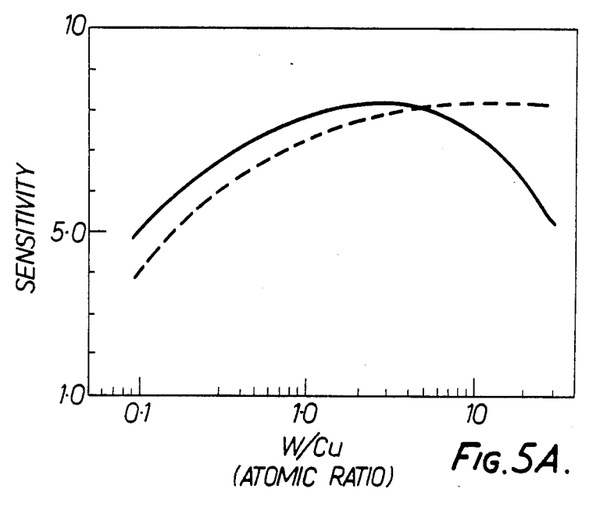
FIG. 5A is a graph showing sensitivity characteristics of the element of the invention for detecting CO gas or tobacco smoke.
Figure 5B:
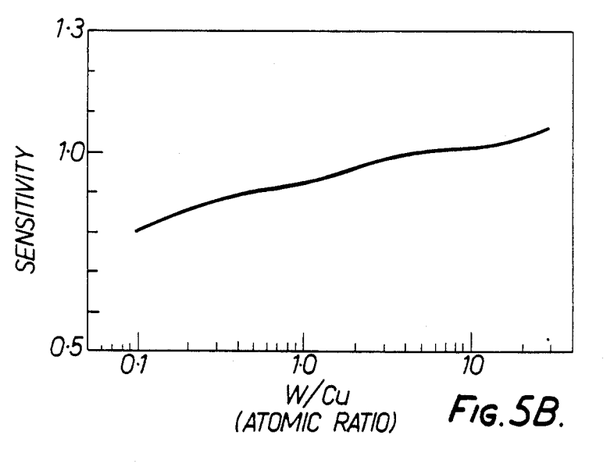
FIG. 5B is a graph showing Ssm/Sco characteristics.

As seen from Table 1, the gas detecting element with a catalyst layer consisting of a carrier and catalyst material of copper and tungsten has the same sensitivity for CO gas with a concentration of 200 ppm and smoke with a concentration of 500 ppm. On the contrary, the gas detecting element containing only copper in the amount of W is less than 0.1 wt%, the sensitivity for both CO gas and tobacco smoke are deteriorated. The difference between the sensitivity for CO gas and that of smoke becomes large when the amount of W exceeds 30 wt%. Thus, the gas detecting element has excellent sensitivity for both CO gas and tobacco smoke when the amount of W ranges 0.1 to 30 wt%. Further, the sensitivity for CO gas and tobacco smoke and the sensitivity ratio of Ssm/Sco are shown in FIGS. 5A and 5B in relation to the amount of the atomic ratio of W/Cu, respectively, wherein the catalyst layer of the element contains 3.0 wt% of W. As seen from FIG. 5A, the gas detecting element has excellent sensitivity for 200 ppm of CO gas (shown in solid line in FIG. 5A) and excellent sensitivity for 500 ppm tobacco smoke (shown in dotted line in FIG. 5A) when the atomic ratio of W/Cu ranges from 0.1 to 10. Still further, as seen from FIG. 5B, the sensitivity ratio Ssm/Sco, which falls within 0.8 to 1.1, is excellent when the ratio of W/Cu ranges between 0.1 to 10.

Figure 6A:
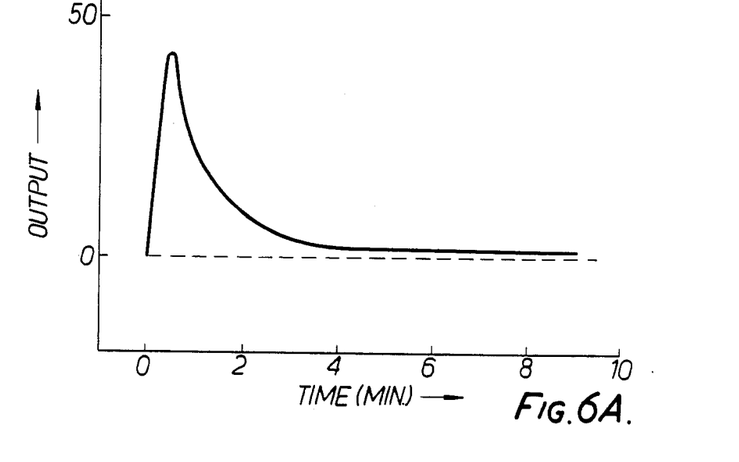
FIG. 6A is a graph showing the humidity characteristics of the element of the invention.
Figure 6B:
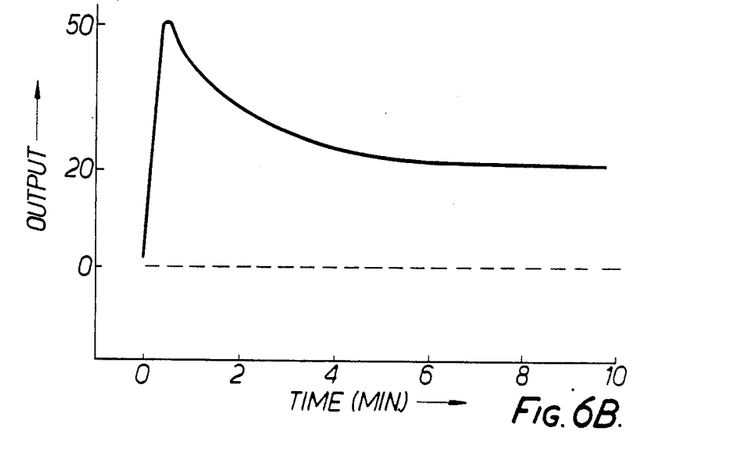
FIG. 6B is a graph showing the humidity characteristics of the element of the comparison examples.

The results of measurements of humidity characteristics are shown in FIGS. 6A and 6B. The measurement is carried out by measuring the output of the gas detecting element after it is left at 90% relative humidity at room temperature. As understood from FIG. 6A showing characteristics of the element of Example 4, the output fluctuation of the element falls within 5% after it settles to a stable condition. On the contrary, as seen from FIG. 6B showing the characteristics of the element of Comparison No. 3, the output fluctuates 20%. Thus, the gas detecting element of the invention has excellent humidity resistance.

Another embodiment of the invention will be explained below. In this embodiment, the gas detecting element has the same construction as that of the gas detecting element shown in FIG. 1 except with respect to the composition of the catalyst layer. Namely, the gas detecting element comprises a cylindrical substrate made of insulating material, a gas sensitive body provided on the substrate which changes its resistance value when it comes into contact with a gas to be detected, a pair of electrodes provided on an outer surface of the substrate so as to contact with the gas sensitive body, and a catalyst layer covering the gas sensitive body. The gas sensitive body with a thickness of about 0.3 microns essentially consists of $SnO_2$. The gas sensitive body is prepared in the same manner explained above.

The catalyst layer with a thickness of 20 microns essentially consists of a carrier material of $Al_2O_3$ and catalyst material of copper sulfate ($CuSO_4$).

The catalyst layer is prepared in the following manner. A predetermined amount of $CuSO_4.5H_2O$ is dissolved in water so that the solution contains 2.0 wt% of Cu and $Al_2O_3$ powder with a surface area of about 100 m$^2$/g is added to the solution. The solution is then stirred. $Al_2O_3$ powder is taken out of the solution by a filter and the powder is dried under a low pressure atmosphere of one and one half hours. After vaporizing water from the powder, the powder is collected. The collected powder is pulverized in a mortar, and the resultant powder is calcined in a quartz crucible at a temperature of 400° C.

A slurry of the catalyst material is obtained by adding the catalyst powder to aluminum hydroxy chloride solution. After the slurry is coated on the gas sensitive body, it is calcined at a temperature of 400° C. A catalyst layer with a thickness of 20 microns, consisting of a carrier material of $Al_2O_3$ and a catalyst material of $CuSO_4$ is prepared.

The sensitivity for CO gas, $H_2$ gas and $C_3H_8$ with a concentration of 200 ppm is measured as the ratio of Rair/Rgas by using the gas detecting element explained above. Rair is the resistance value of the gas detecting element when it is left in an air atmosphere and Rgas is the resistance value of the element when it is left in an atmosphere containing the gas to be detected. Thus, the larger the ratio Rair/Rgas increases, the higher the sensitivity increases. In Table 2, the sensitivity of three kinds of the gas sensitive bodies, each of which comprises $SnO_2$, $SnO_2$-Nb, and $SnO_2$-Sb, respectively, are shown along with the sensitivity of the gas detecting element using a three kinds of catalyst layers, each of which includes 1.0 wt% of Cu, 10.0 wt% of Cu, and 20 wt% of Cu, respectively. During the measurement, the gas sensitivity element is kept at a temperature of about 350° C.

TABLE 2

| Composition of Gas Sensitive Body | Composition of Catalyst Layer | Amount of Cu (wt %) | Sensitivity (R air/R gas) for gas to be detected (Concentration of Each Gas is 200 ppm) | | |
|---|---|---|---|---|---|
| | | | $H_2$ | iso-$C_4H_{10}$ | CO |
| $SnO_2$ | — | — | 2.8 | 2.3 | 1.8 |
| | $CuSO_4$—$Al_2O_3$ | 1.0 | 6.3 | 4.7 | 5.6 |
| | " | 10.0 | 9.7 | 7.5 | 8.2 |
| | " | 20.0 | 6.5 | 6.0 | 7.5 |
| $SnO_2$—Nb | — | — | 3.5 | 2.4 | 2.0 |
| | $CuSO_4$—$Al_2O_3$ | 1.0 | 8.1 | 6.0 | 7.3 |
| | " | 10.0 | 12.2 | 9.5 | 10.2 |
| | " | 20.0 | 8.0 | 7.5 | 9.5 |
| $SnO_2$—Nb | — | — | 4.2 | 2.8 | 2.3 |
| | $CuSO_4$—$Al_2O_3$ | 1.0 | 9.5 | 7.1 | 8.2 |
| | " | 10.0 | 14.1 | 11.3 | 11.8 |
| | " | 20.0 | 9.6 | 9.0 | 11.0 |

As seen from Table 2, the sensitivity of the gas detecting element which does not have the catalyst layer, is low, but the gas detecting element with the catalyst layer of the invention has a high sensitivity compared to the element without the catalyst layer. It is another special feature of the detecting element of the invention that it has substantially the same sensitivity for all gases. Gas detecting elements which contains 1.0 wt% of Cu and 20 wt% of Cu in the catalyst layer tend to decline in sensitivity compared to the elements containing 10 wt% of Cu in the catalyst layer.

Figure 7:
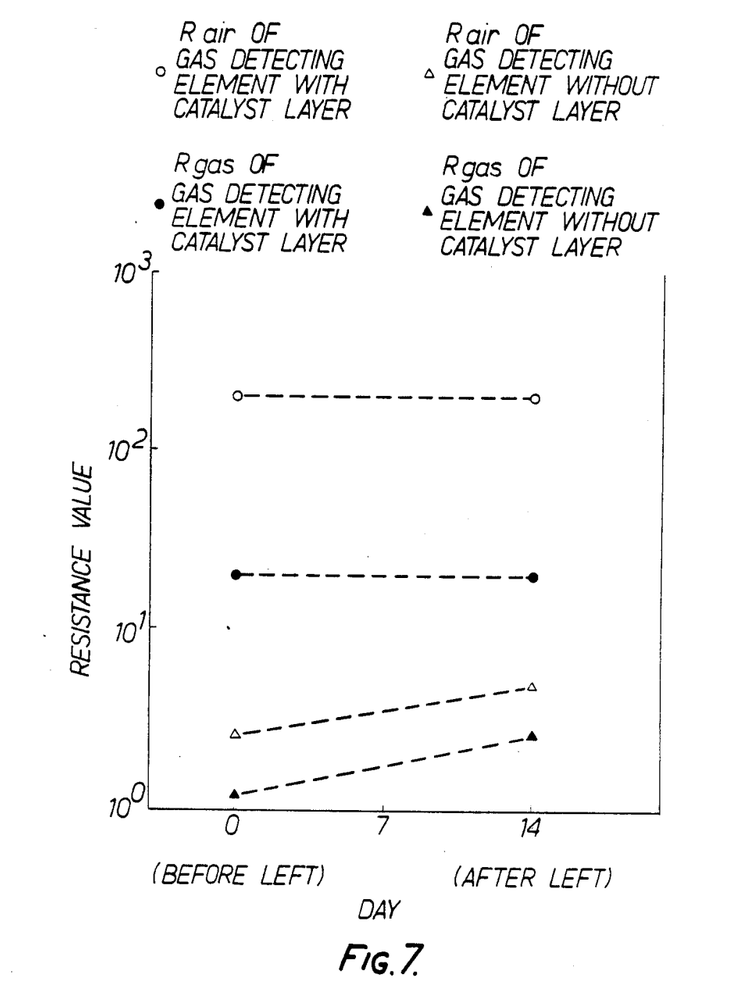
FIG. 7 is a graph showing a resistance value characteristic.

In FIG. 7, the resistance value characteristics of two types of the elements are shown, in which one has a gas sensitive body of $SnO_2$-Nb (referred to as Comparison No. 4 hereafter) and another has a gas sensitive body of $SnO_2$-Nb and the catalyst layer containing material $CuSO_4$ in the amount of 1.0 wt% of Cu, in an atmosphere of air and an atmosphere containing CO gas of 200 ppm. The measurement is carried out after these elements are maintained in an atmosphere with a temperature of 40° C. and a relative humidity of 90 RH% for two weeks. As seen from FIG. 7, the resistance value of Comparison No. 4 fluctuates a great deal compared with its prior resistance value. The resistance value of the element of the invention does not fluctuate at all, however. This means that the gas detecting element of the invention is not affected in its gas detecting characteristics by humidity.

Figure 8:
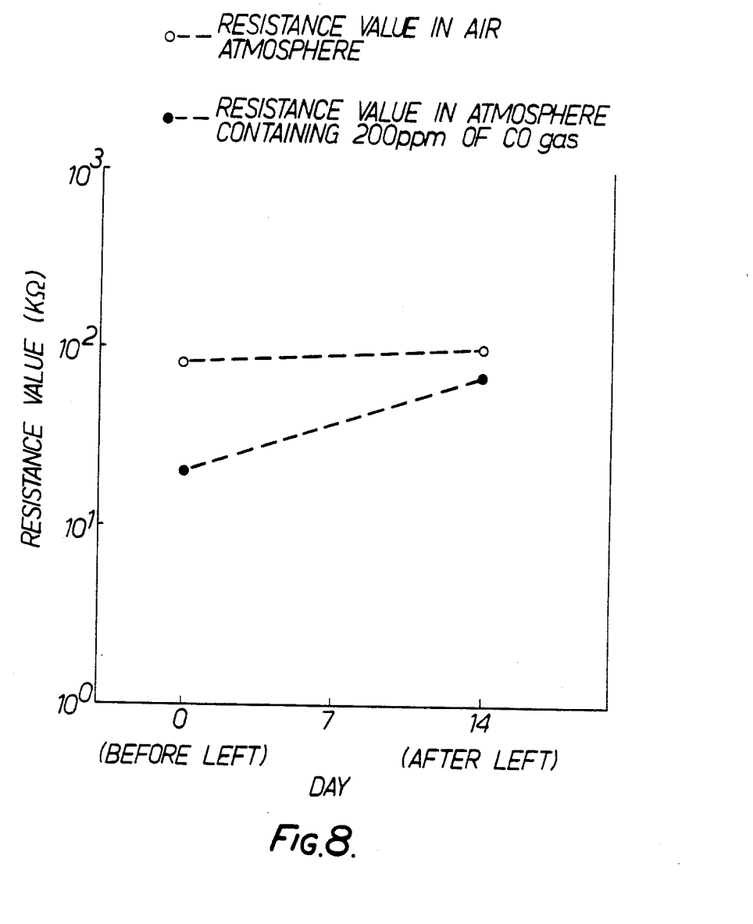
FIG. 8 is a graph showing a resistance value characteristic at high temperature.

FIG. 8 shows resistance value characteristics of a gas detecting element having a gas sensitive body of $SnO_2$-Nb and a catalyst layer consisting of a carrier material of $Al_2O_3$ and a catalyst material of 1 wt% of Rh after it is maintained in a high humidity atmosphere for 14 days. The resistance value is measured when the temperature of the element is about 350° C. As seen from FIG. 8, the resistance value of the element increases after it is maintained in a high humidity atmosphere and the sensitivity for detecting CO gas deteriorates.

It may be noted that many modifications and variations of the above described embodiments will become apparent to those of ordinary skill in the art from a reading of this disclosure. The invention is not limited to the particular device disclosed, its scope is governed only by the scope of the appended claims.

We claim:

1. A gas detecting element comprising:
   a substrate;
   a gas sensitive body of a semiconductor oxide provided on the substrate, the resistance value of the gas sensitive body being changed when said body comes into contact with a gas to be detected;
   a pair of electrodes connected to said gas sensitive body; and
   a catalyst layer provided on a surface of said gas sensitive body, said catalyst layer including a carrier material and catalyst material of copper and tungsten, the atomic ratio of said tungsten to said copper in said catalyst layer being not less than 0.1 and not greater than 10.0.

2. A gas detecting element according to claim 1 wherein said carrier material in said catalyst is aluminum oxide.

3. A gas detecting element according to claim 1 wherein the total amount of said copper and said tungsten ranges from about 0.1 to about 30 wt% as compared with the amount of said carrier material.

4. A gas detecting element according to claim 1 wherein said gas sensitive body is a semiconductor oxide film formed by thermal decomposition of an organic metal.

5. A gas detecting element according to claim 1 wherein said gas sensitive body consists of a $SnO_2$ type semiconductor.

6. A gas detecting element comprising:
   a substrate;
   a gas sensitive body of a semiconductor oxide provided on the substrate, the resistance value of the gas sensitive body being changed when said body comes into contact with a gas to be detected;
   a pair of electrodes connected to said gas sensitive body; and
   a catalyst layer provided on a surface of said gas sensitive body, said catalyst layer including a carrier material and catalyst material of copper sulfate and tungsten.

7. A gas detecting element comprising:
   a substrate,
   a gas sensitive body of a semiconductor oxide provided on said substrate, the resistance value of said gas sensitive body being changed when said body comes in contact with a gas to be detected,
   a pair of electrodes connected to said gas sensitive body, and
   a catalyst layer provided on a surface of said gas sensitive body, said catalyst layer including a carrier material and a catalyst material of copper sulfate ($CuSO_4$).

8. A gas detecting element according to claim 7 wherein said carrier material in said catalyst is aluminum oxide.

9. A gas detecting element according to claim 7 wherein the amount of said copper sulfate ranges from about 0.1 to about 30 wt% compared with the amount of said carrier material.

10. A gas detecting element comprising:
    a substrate;
    a gas sensitive body which essentially consists of an $SnO_2$ type semiconductor provided on said substrate, the resistance value of said gas sensitive body being changed when said body somes into contact with a gas to be detected;
    a pair of electrodes connected to said gas sensitive body; and
    a catalyst layer provided on a surface of said gas sensitive body, said catalyst layer including a carrier material and a catalyst material of copper sulfate ($CuSO_4$).

* * * * *